United States Patent [19]

Gribkoff et al.

[11] Patent Number: 5,621,007
[45] Date of Patent: Apr. 15, 1997

[54] METHOD FOR REGULATION OF TRANSMEMBRANE CHLORIDE CONDUCTANCE

[75] Inventors: Valentin K. Gribkoff, Wallingford; Steven I. Dworetzky, Middletown; Davis L. Temple, Wallingford, all of Conn.

[73] Assignee: Bristol-Myers Squibb Company, New York, N.Y.

[21] Appl. No.: 431,695

[22] Filed: Apr. 28, 1995

Related U.S. Application Data

[63] Continuation of Ser. No. 147,212, Nov. 3, 1993, abandoned.

[51] Int. Cl.$^6$ ............................ A61K 31/415; A61L 9/04
[52] U.S. Cl. .................................. 514/387; 424/45
[58] Field of Search .................. 514/387; 424/45

[56] References Cited

U.S. PATENT DOCUMENTS

| | | | |
|---|---|---|---|
| 5,100,647 | 3/1992 | Agus et al. | 514/286 |
| 5,200,422 | 4/1993 | Olesen et al. | 514/387 |

OTHER PUBLICATIONS

Cotton, C.U., et al., *J. Clin. Invest.*, 79: 80–85 (1987).
Welsh, M.J., *FASEB J.*, 4: 2718–2725 (1990).
Rommens, J.M., et al., *Science*, 245: 1059–1065 (1989).
Riordan, J.R., et al., *Science*, 245: 1066–1072 (1989).
Bear, C., et al., *J. Biol. Chem.*, 266: 19142–19145 (1991).
Higgins, C.F., *Ann. Rev. Cell Biol.*, 8: 67–113 (1992).
Hyde, S.C., et al., *Nature*, 346: 362–365 (1990).
Gabriel, S.E., et al., *Nature*, 363: 263–266 (1993).
Collins, F.S. *Science*, 256: 774–779 (1992).
Kerem, B.S., et al., *Science*, 245: 1073–1080 (1989).
Dalemans, W., et al., *Nature*, 354: 526–528 (1991).
Drumm, M.L., et al., *Science*, 254: 1797–99 (1991).
Gill, D.R., et al., *Cell*, 71: 23–32 (1992).
Valverde, M.A., et al., *Nature*, 355: 830–833 (1992).

*Primary Examiner*—Jerome D. Goldberg

[57] ABSTRACT

Methods for the therapy of cystic fibrosis and multi-drug resistance in cancer chemotherapy by administering to a patient in need thereof 5-trifluoroethyl-1-(5-chloro-2-hydroxyphenyl)-1,3-dehydro-2H-benzimidazol-2-one (NSOO4) or a pharmaceutically acceptable salt thereof.

4 Claims, 3 Drawing Sheets

METHOD FOR REGULATION OF TRANSMEMBRANE CHLORIDE CONDUCTANCE

This is a continuation of application Ser. No. 08/147,212 filed Nov. 3, 1993, now abandoned.

BACKGROUND OF THE INVENTION

1. Field of the Invention

The present invention relates to the use of 5-trifluoromethyl-1-(5-chloro-2-hydroxyphenyl)l,3-dihydro-2 H-benzimidazol-2-one (NSOO4) for therapy of cystic fibrosis and multi-drug resistance in cancer chemotherapy.

2. Background Art

Cystic fibrosis (CF) is a lethal genetic disease afflicting nearly 30,000 people in the United States. In individuals of Northern European extraction, approximately 1 in 2500 newborns is born with the disease, making it the most common lethal, recessively inherited disease among Caucasians (although the disease is present in non-white populations as well). First described in the 1930's, CF was initially thought to be a gastrointestinal disease, as individuals died from malnutrition and inanition (lack of vitality), often in the first year. In particular, the name cystic fibrosis was derived from the original description of the disease as 'cystic fibrosis of the pancreas', which reflected the destruction of pancreatic exocrine function in these patients.

Excessive salt loss occurs in the sweat of children with CF, and the level of sodium and chloride ($Cl^-$) in the sweat was first used as a diagnostic in the 1950's. A decade ago the abnormal levels of salt transport in the sweat of CF patients was attributed to dysfunctional $Cl^-$ transport in sweat ducts, and reduced $Cl^-$ transport in respiratory epithelia was discovered almost simultaneously.

Currently, cystic fibrosis is primarily thought of as a respiratory disease, characterized by airway obstruction due to thick, sticky mucous and serious secondary complications resulting from bacterial infections. Intestinal and pancreatic obstructions and insufficiency are also present in many cases.

Although cystic fibrosis is a single-gene disorder, identification of the gene and gene product(s) responsible for CF proved difficult prior to the discovery that the normal apical epithelial cell $Cl^-$ efflux in respiratory tissues that occurred in response to cAMP stimulation (via β-adrenergic receptor activation) was blunted or absent in CF tissues. This was subsequently shown to reflect a lack of cAMP-dependent protein kinase A-dependent activation of a $Cl^-$ conductance in the epithelial cells. (Cotton, C. U., et al., *J. Clin. Invest.*, 79: 80–85 (1987); Welsh, M. J., *FASEB J.*, 4: 2718–2725 (1990)). These discoveries led to the characterization of the cystic fibrosis transmembrane conductance regulator (CFTR), the gene product responsible for cAMP-activated $Cl^-$ conductance. (Rommens, J. M., et al., *Science*, 245: 1059–1065, (1989); Riordan, J. R., et al., *Science*, 245: 1066–1072 (1989); Bear, C., et al., *J. Biol. Chem.*, 266: 19142–19145 (1991)). The cystic fibrosis transmembrane conductance regulator is a 1480 amino acid protein that is a member of a large family of ATP-binding cassette transporters (ABC transporters) which includes the multi-drug resistance gene (MDR) and its gene product, P-glycoprotein. (Higgins, C. F. *Ann. Rev. Cell Biol.*, 8: 67–113 (1992); Hyde, S. C., et al., *Nature*, 346: 362–365: 1990)). It has now been established that CFTR is a linear $Cl^-$ channel when (a) ATP is bound to two nucleotide binding domains in the protein and (b) cAMP-dependent phosphorylation of a regulatory domain occurs. Recent evidence also suggests that CFTR may control other proteins, including the conductance of an outwardly rectifying $Cl^-$ channel. (Gabriel, S. E., et al., *Nature*, 363: 263–266 (1993)). Many mutations of CFTR have now been reported, many clustered in the first nucleotide binding domain. Included in this group of mutations is the ΔF508 CFTR mutant that is responsible for approximately 70% of CF in the United States. (Collins, F. S., *Science*, 256: 774–779 (1992); Kerem, B. S., et al., *Science*, 245: 1073–1080 (1989)). While it is likely the case that the protein undergoes some degree of temperature-sensitive biosynthetic arrest in cells expressing the ΔF508 CFTR mutant, those channels that are expressed appear to have a deficient response to cAMP stimulation resulting in greatly reduced cAMP-dependent $Cl^-$ current. (Dalemans, W., et al., *Nature*, 354: 526–528 (1991); Drumm, M. L., et al., *Science*, 254: 1797–99 (1991)). Proposed therapies for treating CF therefore include gene therapy to transfect airway epithelial cells with normal CFTR to restore $Cl^-$ function, the development of 'escort' molecules to enhance normal processing of the ΔF508 gene product, and drug therapy to increase $Cl^-$ conductance through mutant CFTR channels or other $Cl^-$ channels that may be under the control of CFTR.

The agent NSOO4, chemically 5-trifluoromethyl-1-(5-chloro-2-hydroxyphenyl)-1,3-dihydro-2 H-benzimidazol-2-one, was disclosed by Olsen, et al, in U.S. Pat. No. 5,200,422 as a member of a series of benzimidazole compounds claimed to be useful in treating diseases which are benefited by the opening of cell membrane potassium channels.

A treatment for cystic fibrosis involving the administration of aerosolized sparteine was disclosed and claimed by Agus, et al, in U.S. Pat. No. 5,100,647. Sparteine chemically is dodecahydro-7,14-methano-2H,6H-di-pyrido[1,2-a;1',2'-e][1,5]diazocine. Agus, et al, describe sparteine as activating chloride channels at low doses but as blocking chloride channels at higher doses. There is nothing in the art to suggest the use of NSOO4, a potassium channel opener, for treating chloride conductance-related disorders such as cystic fibrosis.

SUMMARY OF THE INVENTION

Accordingly, it is an object of this invention to provide a method for the treatment of a disease or other conditions characterized by reduced chloride channel conductance which method comprises administering to a patient suffering therefrom an effective amount of the benzimidazole derivative NSOO4. A related feature is to provide a method for the treatment of cystic fibrosis and multi-drug resistance in cancer chemotherapy.

It is another object of this invention to provide NSOO4 formulations useful in the therapy of cystic fibrosis and multi-drug resistance in cancer chemotherapy.

The above objects, and other objects which will become apparent from the description of the invention given hereinbelow, have now been discovered by the inventors to be satisfied by administering to a patient suffering from either cystic fibrosis or multi-drug resistance an amount of the compound NSOO4 or a pharmaceutically acceptable derivative thereof, effective to provide therapy for cystic fibrosis and multi-drug resistance in cancer chemotherapy. The compound NSOO4 or pharmaceutically acceptable derivatives thereof may be administered to the patient by any known method of administering a pharmaceutical compound, including orally, parenterally, by inhalation spray, or rectally. Of these methods, administration directly to the airway, e.g., as a pressurized aerosol or as a nebulized solution, is preferred for patients with cystic fibrosis.

DETAILED DESCRIPTION OF THE INVENTION

Figure 1A:
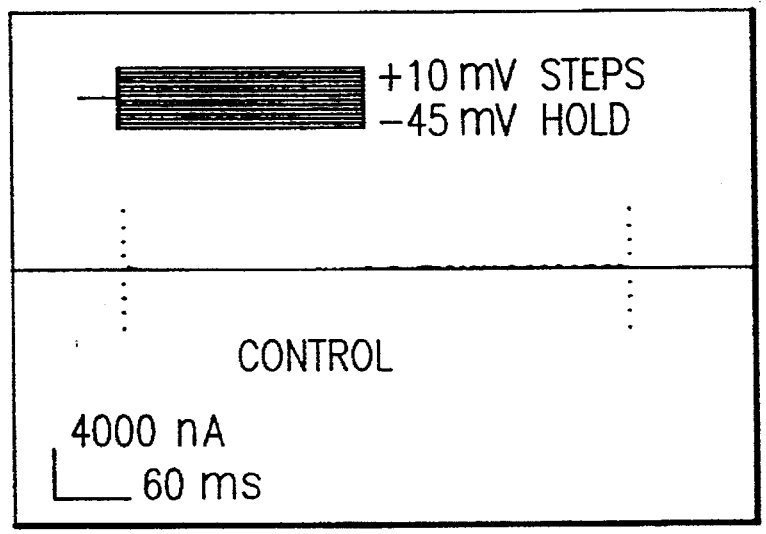
FIG. 1. Shows that the application of NS004 produced a large increase in Cl⁻ current in Xenopus oocytes expressing wild-type CFTR 3 days following injection of CFTR mRNA. This increase in current, which was never seen in uninjected or H$_2$O-injected oocytes, was rapidly reversible.

The subject benzimidazole derivative of the present invention is 5-trifluoromethyl-1-(5-chloro-2-hydroxyphenyl)-1,3-dihydro-2H-benzimidazol-2-one (NS004) having the formula

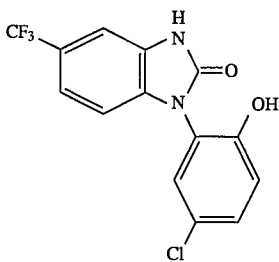

or a pharmaceutically acceptable salt thereof. NSOO4 and related compounds were described in U.S. Pat. No. 5,200,422 issued Apr. 6, 1993 to Olesen, et al, for the treatment of diseases which can be treated by opening cell membrane potassium channels.

The present invention is based on the inventors' discovery that NSOO4 is a very potent modulator of chloride channels. The inventors have discovered specifically that NSOO4 is a very potent activator of chloride channels at low (nanomolar to micromolar) doses.

As an activator of chloride channels, NSOO4 and its pharmaceutically acceptable salts may be used in the therapy of cystic fibrosis and multi-drug resistance in cancer chemotherapy.

The present invention would be a direct-acting drug therapy for CF, because of its ability to directly enhance the opening of mutant and wild-type CFTR Cl⁻ channels and to potentiate the actions of cAMP on mutant channels including ΔF508. In addition it can also provide adjunct treatment in CF gene therapy by enhancing Cl⁻ regulation in transfected epithelial cells, and as adjunct treatment in 'escort' therapy. In the latter case, while such treatment could increase the number of mutant ΔF508 channels present in the epithelial cell membrane in respiratory tissues of CF patients, most present evidence suggests that the regulation of these channels by cAMP via β-adrenergic stimulation would be sub-optimal, a condition that could be largely reversed by drug therapy with compounds that increased the response of the mutant Cl⁻ channels to cAMP.

The multi-drug resistance gene (MDR) product, the P-glycoprotein, is a member of the ABC transporter family that includes CFTR. It is an active transporter, which has as a major function the removal of cytotoxic compounds out of cells. This function of MDR renders cells resistant to cytotoxic agents such as chemotherapeutic agents used in the treatment of cancer. The MDR also functions as a Cl⁻ channel, normally regulated by volume (tonicity). Recent evidence suggests that the transport function of MDR and the Cl⁻ channel function can be separated, and that when functioning in one role, it may not be able to function in its other modality. (Gill, D. R., et al., *Cell*, 71: 23–32 (1992); Valverde, M. A., et al., *Nature*, 355: 830–833 (1992)). It has been shown that while cytotoxic drug application can block MDR's Cl⁻ channel activity, similar applications cannot block Cl⁻ channel activity of a previously activated channel. This suggests that increasing the opening of the channel by Cl⁻ channel openers, particularly those that act on ABC transporter-associated Cl⁻ channels, may reduce drug resistance in affected cells. This method of use invention is also intended to provide adjunct therapy against the acquisition of oncolytic drug resistance in patients receiving cancer chemotherapy.

The present invention flows from the discovery that a Maxi-K potassium channel opening agent, designated in the literature as NSOO4, significantly increases chloride conductance in certain chloride channel cellular structures. Of particular significance is the effect on chloride conductance by NSOO4 at the Cystic Fibrosis Transmembrane Conductance Regulator (CFTR), its mutated forms, and the Multi-Drug Resistance gene (MDR) chloride channel/drug transporter.

The pharmaceutically acceptable salts which can be used in accordance with the invention include pharmaceutically acceptable salts derived from inorganic or organic acids. Included among such salts are the following: sulfate, adipate, alginate, asparate, benzoate, benzenesulfonate, busulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxymethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecenoate.

The compositions of the present invention may be administered orally, parenterally, or by inhalation spray, in dosage unit formulations containing conventional non-toxic pharmaceutically acceptable carriers, adjuvants and vehicles as known in this art. The term parenteral as used herein includes subcutaneous injections, intravenous, intramuscular, intrasternal injection or infusion techniques.

A specific advantage of the present invention, in its application to cystic fibrosis, is the delivery of the active agent to the airway epithelia (the cells which exhibit impaired chloride transport in cystic fibrosis) by aerosol. This eliminates the need for systemic therapy and bypasses potential toxicity from other effects (such as alteration of potassium levels).

Thus, for the therapy of cystic fibrosis in accordance with a preferred embodiment of the present invention, NSOO4 or a pharmaceutically acceptable salt thereof, is preferably directly administered to the patient's lungs, either as a pressurized aerosol or as a nebulized solution. Solutions for administration by nebulization are preferably aqueous solutions designed to provide a final concentration of 0.05 to 1.0, preferably to 0.2, nanomolar (nM) at the airway surface. But the concentration used depends, of course, among other factors, on the severity of the disease. In cystic fibrosis patients, this may depend on the particular mutation exhibited by a particular patient.

The dosage for administration of the active ingredient, NSOO4, for the therapy of cystic fibrosis or multi-drug resistance in accordance with the present invention varies with, among other factors, the method of administration, and the severity of the disease. In general, an oral dosage of from about 1.0 to 100 milligrams, designed to produce a blood level of 10 to 200 nM, administered one to eight, preferably two to six, and most preferably two to four times a day, is satisfactory. A preferred total daily dosage for adult patients is from about 4 to 400 milligrams, preferably from 2 to 200 milligrams. For children, especially infants, the daily dosage used would be at the lower end of this range, or even less than in certain cases. In general, for cystic fibrosis, the treatments may be continued for a period of several months or years, possibly throughout the cystic fibrosis patient's lifetime. To treat multi-drug resistance, treatment would be concomitant with cancer chemotherapy.

In accordance with a preferred embodiment of the present invention, NS004 or a pharmaceutically acceptable salt thereof, is presented as a medicinal aerosol formulation permitting its administration directly to the cystic fibrosis patient's lungs. In particular, this medicinal aerosol formulation may contain known aerosol propellants, including chlorofluorocarbon aerosol propellants known useful for endopulmonary and/or nasal inhalation administration. Such medicinal aerosol formulations generally contain a mixture of chlorofluorocarbons, for example, trichloromonofluoromethane (propellent 11), dichlorotetrafluoroethane (propellent 114) or dichlorodifluoromethane (propellant 12). The active ingredient is present as a solution in the aerosol formulation.

In addition to the active ingredient and water, the aqueous solutions may contain co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin polyethylene glycol 300, and 400, propylene glycol, sorbitol, polyoxyethylene sorbitan fatty acid esters such as laureate, a palmitate, stearate, and oleate, polyoxyethylated vegetable oil, sorbitan monopalmitate, 2-pyrrolidone; n-methyl-2-pyrrolidine; n-ethyl-1-pyrrolidine and tetrahydrofuryl alcohol.

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8 wt. %), ascorbic acid (0.05–1.0 wt. %), monothioglycerol (0.1–1.0 wt. %) potassium metabisulfite (0.01–1.0 wt. %), sodium formaldehyde sulfoxylate (0.03–0.1 wt. %), sodium metabisulfite (0.02–0.25 wt. %), sodium sulfite (0.01–0.1 wt. %), sodium thioglycolate (0.03–0.1 wt. %).

Examples of chelating/complexing agents and typical concentration ranges include edentate sodium (0.005–0.1 wt. %), edentate calcium disodium (0.005–0.01 wt %) gentisic acid ethanolamide (1.0–2.0 wt. %), niacinamide (1.0–2.5 wt. %), sodium citrate (0.01–2.5 wt. %), citric acid (0.001–1.0 wt. %).

Examples of inert gases are nitrogen and carbon dioxide. Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH-dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, and carbonic and bicarbonic; and their corresponding salts such as: potassium, sodium, magnesium, calcium and diethanolamine salts.

Osmolality is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution is to be dispensed from multiple dose containers, antimicrobial agents in bacteriostatic or fungistatic concentrations must be added. Among the compounds and concentrations most frequently employed are phenylmercuric acid (0.002–0.1 wt. %), thimerosal (0.01 wt. %), benzethonium chloride (0.01 wt. %), benzalkonium chloride (0.02 wt. %), phenol or cresol (0.5 wt. %), chlorbutanol (0.5 wt. %), benzyl alcohol (2.0 wt. %), methyl p-hydroxybenzoate (0.18 wt. %), and propyl p-hydroxybenzoate (0.02 wt. %).

After the solution of the active ingredient with its solvents and additives has been compounded, the solution is filtered to remove particulate matter above 2 μm in size and a further step eliminating particulate matter down to 0.2 μm can remove microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

In another embodiment, the pharmaceutical compositions containing the active ingredient in accordance with the invention may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents in order to provided a pharmaceutically elegant and palatable preparation.

Tablets containing the active ingredient in admixture with non-toxic pharmaceutically acceptable excipients which are suitable for manufacture of tablets may be used. These excipients may be, for example, inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

All publications cited in this specification are indicative of the level of skill of those in the art to which this application pertains. Each publication is individually incorporated herein by reference in the location where it is cited.

Having generally described this invention, a further understanding can be obtained by reference to certain specific examples which are provided herein for purposes of illustration only and are not intended to be limiting unless otherwise specified.

EXAMPLES

Heterologous Xenopus Oocyte Expression System

The CFTR and CFTRΔF508 genes were subcloned into the Bluescript vector. The plasmids were linearized with the restriction enzyme SalI which resides downstream of the cDNA insert and in vitro transcribed using T7 polymerase in the presence of the cap analog 5',7-methyl Gppp 5'G. Template DNA was digested with RNase-free DNaseI and the cRNA was phenol-chloroform extracted and precipitated with ammonium acetate and ethanol. The cRNA was rinsed with 70% ethanol, vacuum dried, and solubilized in RNase-free water and stored at −70° C. at a concentration of 1 µg/µl.

Oocytes were surgically removed from *Xenopus laevis* anesthetized with 0.12% 3-aminobenzoic acid ethyl ester (Tricaine). Oocytes were first rinsed with $Ca^{2+}$-free OR2 medium (82.5 mM NaCl, 1 mM KCl, 1 mM $MgCl_2$, 5 mM HEPES, pH 7.5 with NaOH) followed by incubation in collagenase (1.5 mg/ml prepared in $Ca^{2+}$-free OR2 medium) for 4 hours at room temperature. After enzyme treatment, cells were rinsed 8× with OR2 medium and then rinsed again 8× with ND96 medium (90 mM NaCl, 1 mM KCl, 1 mM $CaCl_2$, 1 mM $MgCl_2$, 5 mM HEPES, pH 7.5 with NaOH). Oocytes were stored overnight at 17° C. Late stage V and early stage VI cells that were visualized to be fully defolliculated to the vitelline envelope were selected for microinjection.

Approximately 50 nl of cRNA encoding the wild type 6.2 CFTR gene or the 6.2ΔF508 gene were microinjected into the cytoplasm of the oocyte and incubated 3–10 days for ion channel expression and subsequent electrophysiological evaluation.

Electrophysiological evaluation of the effects of putative CFTR openers were assessed in oocytes expressing wild-type and ΔF508 CFTR constructs using standard two-electrode voltage clamp techniques. Generally, a family of currents was generated under control conditions (incubated in Modified Barth's Solution, MBS, a typical physiological saline medium, in the absence of drugs), with no current or small currents generated under drug-free conditions. The holding potential was −25 or −45 mV, and voltage steps of greater than 200 ms and 20 mV step amplitude were applied starting at approximately −120 mV and ending at approximately +60 mV. All drugs were applied in the bath; solutions were prepared in the normal MBS incubation medium, and applied to the recording chamber by switching the solution lines. Subsequent experimental protocols involved testing the effects of a cAMP 'cocktail' [consisting of the cAMP-elevating agent forskolin (5 μM), db-cAMP (a membrane permeant form of cAMP; 100 μM), and the phosphodiesterase inhibitor isobutylmethylxanthine (IBMX; 100 μM)], or NS004 at various concentrations, or the cAMP 'cocktail' and NS004 simultaneously, on the responses to identical voltage clamp protocols. Whenever possible, oocytes were re-exposed to control conditions to determine reversibility of drug effects. Data were collected and analyzed using a computer equipped with an A/D interface and appropriate acquisition and analysis software.

Cultured Vero Cell—Vaccinia Virus Co-expression System

The second method employed for the expression of wild-type and mutant CFTR constructs was a vaccinia virus co-expression system. In this system an initial virus infection of host cells produces constitutive expression of the phage T7 RNA polymerase under control of the VV7.5K promoter (VVTG1193), and a second virus infection of the host cells produces expression of the coding region of the CFTR cDNA or the ΔF508 CFTR mutant cDNA, under control of the T7 promoters VVTG5959 and VVTG5968, respectively. Coinfection was carried out in Vero cells, a monkey kidney fibroblast cell line.

Electrophysiological and biochemical techniques were used to determine if the claimed compound increased Cl⁻ conductance through the CFTR channel and its mutated ΔF508 homolog. To determine effects of experimental manipulations on Cl⁻ flux Vero cells were pre-incubated in $^{125}$I (iodine passes through Cl⁻ channels, and hence can be used as a measure of Cl⁻ flux). Subsequently, various concentrations of NS004 were tested for direct effects on $^{125}$I efflux in cells expressing wild-type and ΔF508 CFTR constructs, the ability of NS004 to affect the anion efflux stimulated by cAMP (produced by application of Forskolin) was also tested. In addition, both whole-cell and single-channel (outside-out) patch clamp configurations were employed to directly determine the effects of cAMP (produced by addition of Forskolin), NS004, and the combination of cAMP and NS004 on whole-cell and single channel Cl⁻ currents in infected Vero cells under nominally sodium and potassium-free conditions. In all cases data were collected and analyzed by computer.

Figure 1B:
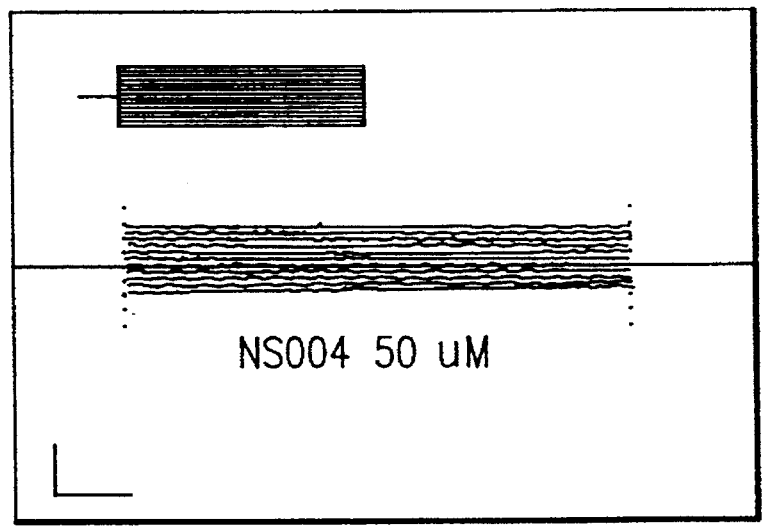
Figure 1C:
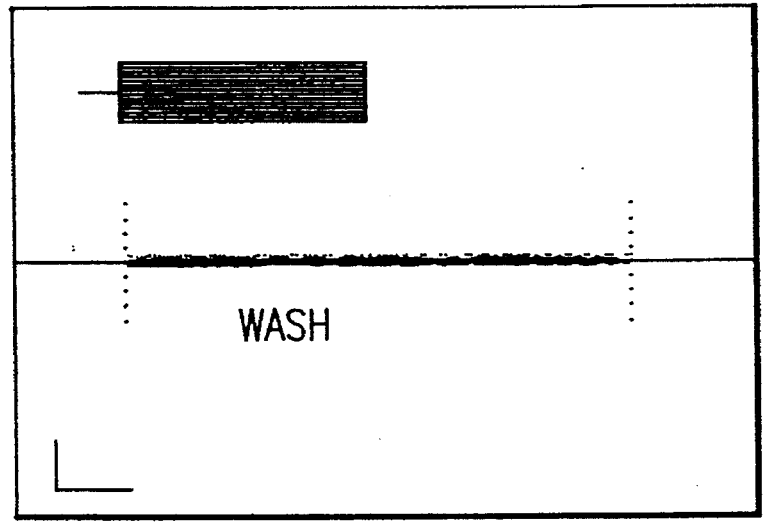

NS004 has been shown by the inventors to reversibly open the unstimulated wild-type CFTR in the heterologous Xenopus oocyte expression system with great efficacy, and potency in the sub-micromolar to micromolar concentration range (e.g. FIG. 1). In the wild-type CFTR expressed in this system, addition of NS004 to the cAMP-stimulated channel produced only a marginal enhancement of chloride current. In oocytes expressing the ΔF508 deletion mutant of CFTR, NS004 produced only a small enhancement of chloride current when applied alone, but greatly exacerbated the level of cAMP stimulation of channel activity, as revealed by two-electrode voltage clamp, when simultaneously applied with cAMP and related agents. The normally very slow time course of cAMP-stimulated chloride current increase in the oocytes expressing ΔF508 mutants was greatly reduced (response time enhanced) in the presence of both cAMP and NS004.

Figure 2A:
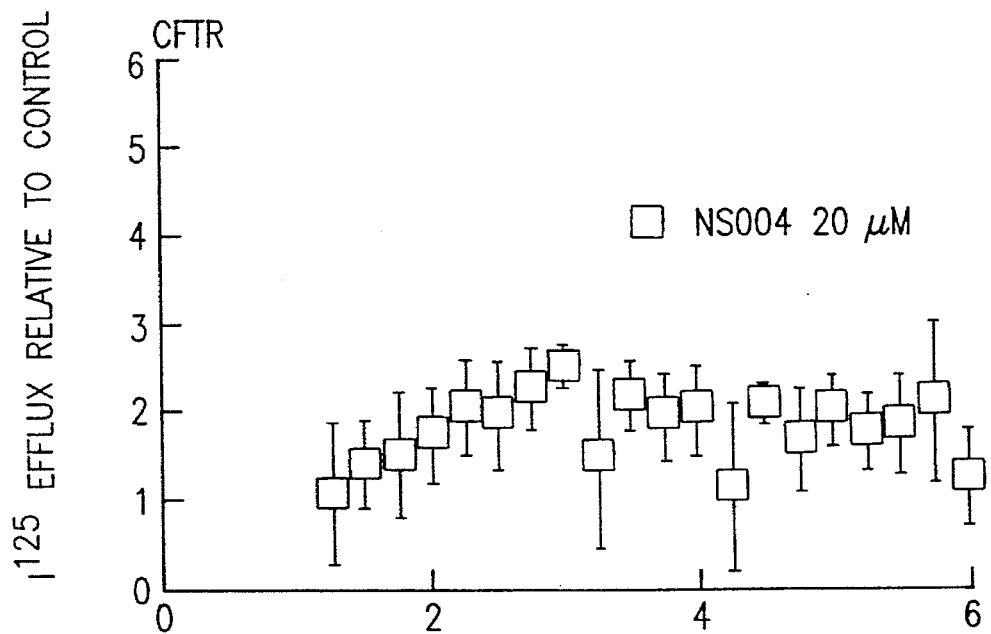
FIG. 2. Shows that in Vero cells expressing CFTR (upper panel) and ΔF508 mutant CFTR (lower panel) constructs, $^{125}$I efflux was increased relative to control by NS004 20 μM (shown only for CFTR), and the increase in efflux elicited by cAMP (produced by application of 5 μM Forskolin) was greatly potentiated by coapplication of cAMP and NS004 in cells expressing ΔF508 CFTR.
Figure 2B:
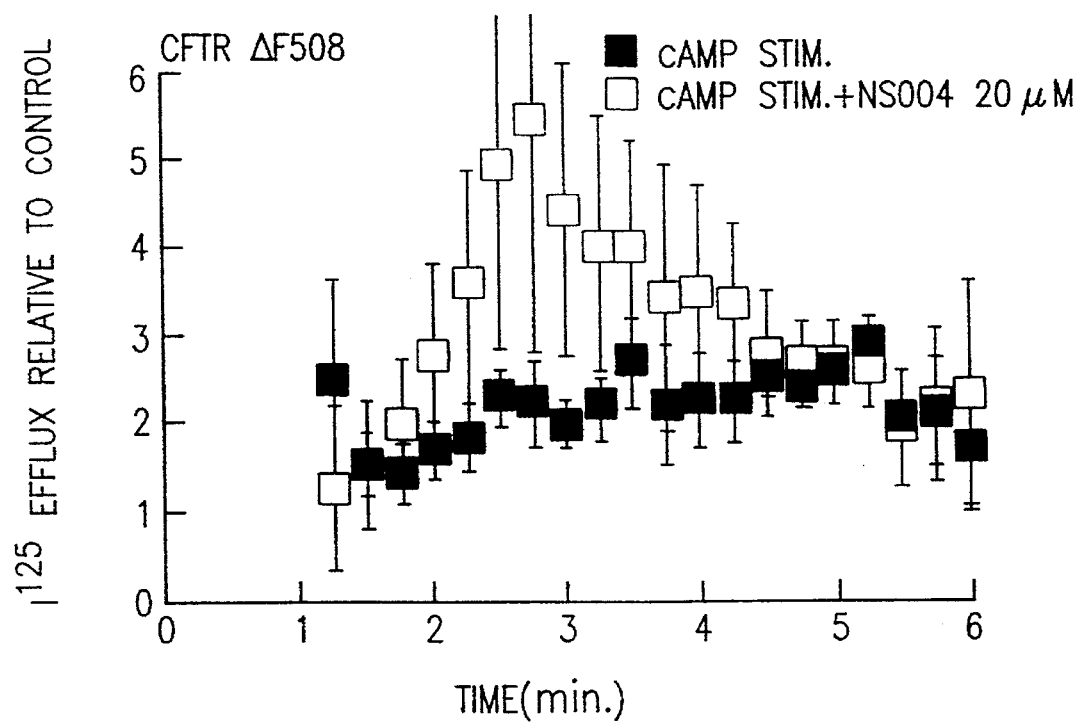
Figure 3:
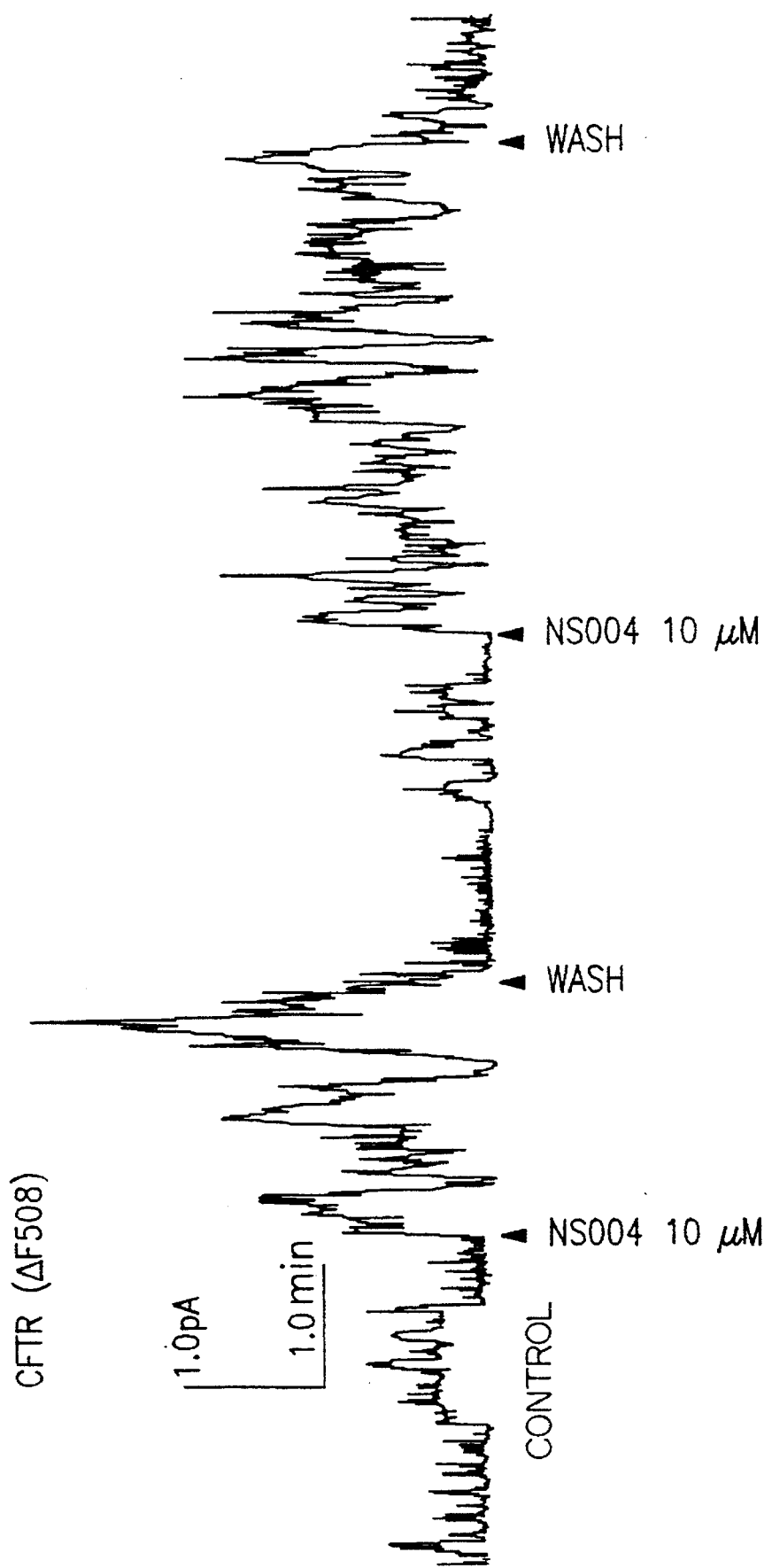
FIG. 3. Shows that in an excised outside-out patch from the membrane of a Vero cell expressing ΔF508 mutant CFTR Cl⁻ channels, NS004 produced a rapid and reversible direct increase in the opening of these channels. Control cells (not expressing CFTR constructs) did not exhibit cAMP-sensitive channels, and did not respond to drug application.

Other experiments have tested the effects of NS004 on $^{125}$I-flux from Vero cells previously virally-infected with constructs producing expression of the wild-type CFTR and the ΔF508 CFTR. The results of these experiments have been consistent with previous experiments utilizing oocytes; in cells expressing wild-type CFTR, $^{125}$I-flux was increased modestly over control values in the 0.1–20 micromolar concentration range, and addition of both cAMP and NS004 did not significantly increase total anion flux. In cells expressing the mutant channels, $I^{125}$-flux was only marginally effected by direct application of NS004 alone, but the compound greatly enhanced the amplitude and reduced the slow time course of the increase in anion flux produced by cAMP (FIG. 2). In mock transfected cells (initial viral infection with T7 only, with no subsequent CFTR infection and expression), no response to cAMP or NS004 was observed on $^{125}$I efflux. In the whole-cell patch clamp configuration, NS004 produced large to moderate increases in the whole cell inward and outward Cl⁻ current when applied alone at the concentrations used in the flux experiments in Vero cells expressing either the wild-type and ΔF508 CFTR constructs. In cells expressing the wild-type CFTR, the combination of CAMP stimulation and NS004 produced only marginal increases in current relative to the values obtained in cAMP alone, but in cells expressing the ΔF508 CFTR, NS004 potently potentiated the maximal stimulation of Cl⁻ current by cAMP, and greatly enhanced the response time to peak. In mock transfected cells, no effects of cAMP or NS004 were observed under these experimental conditions. In outside-out single channel recordings, sub-micromolar to micromolar NS004 potently and directly opened Cl⁻ channels in patches excised from cells expressing either the wild-type or ΔF508 mutated form of CFTR (FIG. 3).

The benzimidazolone agent NS004 produced a significant increase in the Cl⁻ current attributable to expression of CFTR in Xenopus oocytes and in virus-infected Vero cells. A smaller direct increase in whole cell Cl⁻ current was produced by NS004 in oocytes and Vero cells expressing the ΔF508 mutant CFTR construct. NS004 produced a profound potentiation of cAMP stimulation of Cl⁻ current in cells expressing the mutant channels, but only a small potentiation of cAMP-stimulated current in cells expressing the wild-type CFTR construct. The compound greatly increased the open probability of single wild-type and ΔF508 CFTR Cl⁻ channels in infected Vero cells in outside-out excised patches. In infected Vero cells pre-incubated with $^{125}$I, NS004 produced only modest direct increases in $^{125}$I efflux in cells infected with both wild-type and ΔF508 CFTR constructs, but in cells expressing mutant channels, co-administration of cAMP and NS004 produced a robust potentiation of $^{125}$I efflux, such that the levels of efflux attained were comparable to the efflux stimulated by cAMP in cells expressing wild-type CFTR.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A method for the treatment of a disorder characterized by reduced chlorine channel conductance with the disorder being cystic fibrosis, the method comprising administering to a patient suffering from such a disorder, an effective amount of the compound 5-trifluoromethyl-1-(5-chloro-2-hydroxyphenyl)-1,3-dihydro-2H-benzimidazol-2-one or a pharmaceutically acceptable salt thereof.

2. A method for the treatment of a disorder characterized by reduced chlorine channel conductance with the disorder being cystic fibrosis, the method comprising pulmonary administration by aerosol spray to a patient suffering from such a disorder, the aerosol spray formulation comprising an effective amount of 5-trifluoromethyl-1-(5-chloro-2-hydroxyphenyl-1,3-dihydro-2H-benzimidazol-2-one or a pharmaceutically acceptable salt thereof in a non-toxic pharmaceutically acceptable carrier, adjuvant or vehicle suitable for aerosol application.

3. The method of claim 3 wherein the aerosol spray formulation is suitable for administration as an aerosol or by nebulization.

4. The method of claim 3 wherein the aerosol spray formulation is administered as a pressurized aerosol.

* * * * *